United States Patent
Silver (10) Patent No.: US 9,538,975 B2
(45) Date of Patent: Jan. 10, 2017

(54) SCATTER CORRECTION METHOD AND APPARATUS FOR COMPUTED TOMOGRAPHY IMAGING

(71) Applicant: TOSHIBA MEDICAL SYSTEMS CORPORATION, Otawara-Shi (JP)

(72) Inventor: Michael D. Silver, Northbrook, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 96 days.

(21) Appl. No.: 14/681,778

(22) Filed: Apr. 8, 2015

(65) Prior Publication Data
US 2016/0296191 A1    Oct. 13, 2016

(51) Int. Cl.
*A61B 6/03* (2006.01)
*A61B 6/00* (2006.01)
*G06T 11/00* (2006.01)
*G06T 7/00* (2006.01)

(52) U.S. Cl.
CPC ............ *A61B 6/5282* (2013.01); *A61B 6/032* (2013.01); *G06T 7/0012* (2013.01); *G06T 11/005* (2013.01); *G06T 2207/10081* (2013.01)

(58) Field of Classification Search
CPC ......... A61B 6/03; A61B 6/032; A61B 6/5282; G06T 7/00; G06T 7/001; G06T 7/002; G06T 7/0012; G06T 11/00; G06T 11/003; G06T 11/005; G01N 23/04
See application file for complete search history.

(56) References Cited

U.S. PATENT DOCUMENTS

| 7,192,180 B2 * | 3/2007 | Hayek | G04B 15/06 368/124 |
| 2008/0075347 A1 * | 3/2008 | Ruhrnschopf | G06T 11/005 382/131 |
| 2010/0027867 A1 * | 2/2010 | Bernhardt | A61B 6/00 382/132 |

OTHER PUBLICATIONS

Ohnesorge et al, "Efficent Object Scatter Correction Algorithm for Third and Fourth Generation CT Scanners", Eur. Radiol. 9, 563-569 (1999).*

* cited by examiner

*Primary Examiner* — David E Smith
(74) *Attorney, Agent, or Firm* — Oblon, McClelland, Maier & Neustadt, L.L.P.

(57) ABSTRACT

A method and apparatus to correct for scatter in projection data by successive approximations of a primary-beam estimate and a scatter estimate. The scatter estimate is calculated by convolving a scattering function, which is a function of the primary-beam estimate, with a smoothing function that includes Rayleigh scattering and Compton scattering terms. The scattering function is greater than zero in the limit that the primary-beam estimate goes to zero. The projection data can be X-ray computed tomography projection data, and the choice of scattering function has the benefit of reducing dark-band artefacts in reconstructed computed tomography images.

18 Claims, 6 Drawing Sheets

SCATTER CORRECTION METHOD AND APPARATUS FOR COMPUTED TOMOGRAPHY IMAGING

BACKGROUND

Field

Embodiments described herein relate generally to a method of scatter correction of projection data, and more specifically to a method of scatter correction of X-ray projection data in a computed tomography scanner system.

Description of the Related Art

In general, an X-ray projection image contains many scattered radiation components. This scattered radiation greatly degrades the accuracy of a computed tomography (CT) value in three-dimensional imaging using a two-dimensional detector. A two-dimensional detector, like a flat-panel detector used in an X-ray diagnostic apparatus, uses a scattered-radiation-removing grid to suppress scattered radiation. The suppression of scattered radiation can be further improved by post processing the projection data using a scatter-correction algorithm. In an X-ray computed tomographic apparatus, a scatter-correction algorithm in conjunction with a scatter-suppressing grid yields superior images compared to scatter-suppressing grids alone because of residual scatter. Scattered radiation correction is indispensable for extracting low-contrast information, e.g., for imaging soft tissue, by using three-dimensional imaging using a two-dimensional detector.

In addition to the examples given above that discuss scatter scatter-suppressing grids and scattered radiation correction to improve the image quality of projection images and that also discuss improving the image quality of reconstructed images obtained from computed tomography on a series of projection images at different projection angles, scatter suppression can also be important for measurement geometries other than three-dimensional CT imaging using a two-dimensional detector. For example, the concepts and methods discussed herein also apply to a measurement geometry of two-dimensional CT imaging using a one-dimensional detector. The method of scatter correction can also apply when the projection data is not used for CT reconstruction.

An X-ray beam in the presence of a scattering object can be modeled as a primary X-ray beam $P(x, y)$ and a scattered X-ray beam $S(x, y)$, wherein the projection data $T(x, y)$ is a composite of these two:

$$T(x,y)=P(x,y)+S(x,y).$$

Using a forward-scatter model, the scattered radiation $S(x, y)$ is given by $$S(x,y)=SF(P(x,y))*G_2(x,y),$$

where $$SF(X)=-X \log(X), \text{ and}$$

$$G_2(x,y)=A_1\exp[-\alpha_1(x^2+y^2)]+A_2\exp[-\alpha_2(x^2+y^2)]$$

is a smoothing function that is a double Gaussian kernel with one term representing the coherent (Rayleigh) scattering and the other term representing the incoherent (Compton) scattering. The symbol "*" represents a convolution operator. The term with the coefficient $A_1$ is obtained by modeling Rayleigh scattering, and the term with the coefficient $A_2$ is obtained by modeling Compton scattering. In addition to expressing the physics of Rayleigh and Compton scattering, the double Gaussian kernel also expresses factors such as the geometry of the imaging device and the effectiveness of the scatter-suppressing grids. For example, the values of $\alpha_1$ and $\alpha_2$ depend on the aspect ratio of the scatter-suppressing grids. The "aspect ratio" is the height of the grid to its opening. In one implementation, in C-arm ASGs (anti-scatter grids) the aspect ratio can be approximately 10:1; while in diagnostic CT-scanners the aspect ratio can be approximately 30:1. These illustrative aspects ratios are non-limiting examples.

Given the above expressions, the total beam $T(x, y)$ can be directly calculated from a known primary beam $P(x, y)$, but it is impossible to analytically calculate the primary beam $P(x, y)$ from a known total beam $T(x, y)$. A conventional technique, therefore, calculates an estimate of the primary beam $P_g (x, y)$ by minimizing $$E=|T(x,y)-T_g(X,y)|$$

using a successive approximation method, where $T_g(x, y)$ is a composite image calculated based on $P_g(x, y)$, and can be represented by $$T_g(x,y)=P_g(x,y)+S_g(x,y),$$

where $S_g(x, y)=-P_g(x, y) \log P_g(x, y)*G_2 (x, y)$, as discussed in U.S. Pat. No. 7,912,180, the contents of which are incorporated herein by reference.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

In one embodiment, there is provided an apparatus for scatter correction of projection data, the apparatus comprising processing circuitry configured to: (1) calculate a primary-beam estimate $P^n$, and (2) calculate a scatter estimate $S^n$ using a convolution between a scattering function, $SF(P^n)$, and a smoothing function G, wherein $P^n$ is a current primary-beam estimate, $S^n$ is a current scatter estimate, and $SF(P^n)$ is a predetermined scatter function that is a function of the current the primary-beam estimate and is greater than zero over the range $0 \leq P^n < 1$.

In another embodiment, the processing circuitry is further configured calculate the primary-beam estimate according to $$P^n = \frac{P^{n-1}T}{P^{n-1} + S^{n-1}},$$

wherein $P^{n-1}$ is a previous value of the primary-beam estimate, $S^{n-1}$ is a previous value of the scatter estimate, and T is the projection data.

In another embodiment, the processing circuitry is further configured to calculate the scattered estimate using the predetermined scatter function, which is given by $$SF(P^n) = \begin{cases} -(\log(P_1)+1)P^n + P_1 & P^n < P_1 \\ -P^n \log(P^n) & P^n \geq P_1 \end{cases},$$

wherein $P_1$ is a predefined value between zero and one.

In one embodiment, the smoothing function is given by $$G(x,y)=A_1\exp[-\alpha_1(x^2+y^2)]+A_2\exp[-\alpha_2(x^2+y^2)],$$

wherein $A_1$, $\alpha_1$, $A_2$, and $\alpha_2$ are predetermined values.

In another embodiment, the processing circuitry is further configured to perform an iterative loop, wherein each iteration of the iterative loop includes the calculation of the primary-beam estimate and the calculation of the scatter estimate. The processing circuitry is further configured to stop the iterative loop when a predefined convergence criterion is satisfied.

Figure 1:
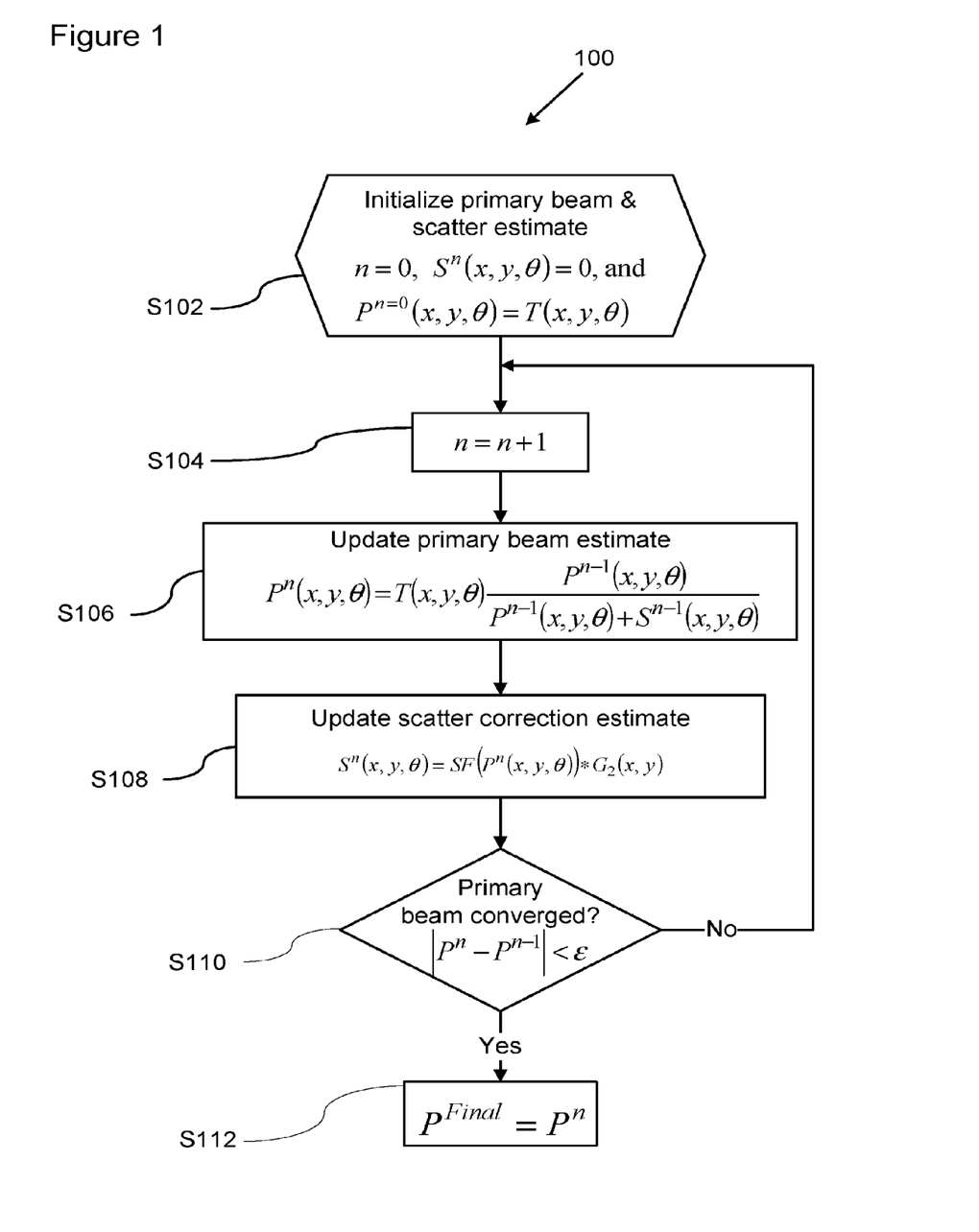
FIG. 1 shows a flow diagram of an implementation of a scatter-correction method.

Referring now to the drawings, wherein like reference numerals designate identical or corresponding parts throughout the several views, FIG. 1 shows an iterative scatter correction method 100 to extract a primary beam $P(x, y, \theta)$ from projection data $T(x, y, \theta)$ in the presence of scatter $S(x, y, \theta)$. The angle $\theta$ designates the direction in which a projection measurement is made, and x and y are the locations of the detectors detecting the projection data. Absent scatter (i.e., when the primary beam $P(x, y, \theta)$ equals the projection data $T(x, y, \theta)$) the projection data is given by $$T(x,y,\theta)=\int dE I_0(E)\exp[-\int dl(x,y,\theta)\mu(l,E)l],$$

where E is the X-ray energy, $I_0(E)$ is the incident intensity as a function of energy spectrum of the X-ray beam, $\mu(l, E)$ is the X-ray absorption coefficient as a function of energy E and the position l, and $l(x, y, \theta)$ is the position along the trajectory of the ray ending at the detector element at position $(x, y)$ when the projection angle is $\theta$. When the X-ray beam can be approximated as mono-chromatic, then the absorption can be obtained by a log-conversion step to obtain $$\int dl\mu l = -\log(T/I_0).$$

In the context of image reconstruction, the phrase "projection data" refers to the raw data after undergoing the log-conversion step because the absorption rather than the intensity/irradiance is used for CT image reconstruction. The phrase "projection data" can also be used to describe the intensity/irradiance measurements prior to the log-conversion step, resulting in ambiguity unless the context is clearly specified in which the phrase "projection data" is used. Here, "projection data" means the intensity/irradiance measurements prior to the log-conversion because the discussion herein focuses primarily on scatter correction and focuses less on the actual image reconstruction. Here, the discussion also assumes, without loss of generality, that the primary beam $P(x, y, \theta)$, projection data $T(x, y, \theta)$, and scatter $S(x, y, \theta)$ are each normalized by the incident intensity, such that (except for the unlikely case that the imaged object exhibits gain at X-ray frequencies or the scatter exceeds absorption over some regions) each of the primary beam $P(x, y, \theta)$, projection data $T(x, y, \theta)$, and scatter $S(x, y, \theta)$ will have values between zero and one.

In FIG. 1, the method 100 begins with step S102 by initializing the loop variable n and initializing the scatter estimate $S^n(x, y, \theta)$ and primary beam estimate $P^n(x, y, \theta)$.

The second step S104 of method 100 increments the loop variable n.

The third step S106 of method 100 uses the previous estimates of the scatter $S^{n-1}(x, y, \theta)$ and the previous primary beam $P^{n-1}(x, y, \theta)$ to update the primary beam estimate in order to obtain the current primary beam estimate $P^n(x, y, \theta)$ using the expression $$P^n(x,y,\theta)=T(x,y,\theta)\frac{P^{n-1}(x,y,\theta)}{P^{n-1}(x,y,\theta)+S^{n-1}(x,y,\theta)}.$$

Figure 4:
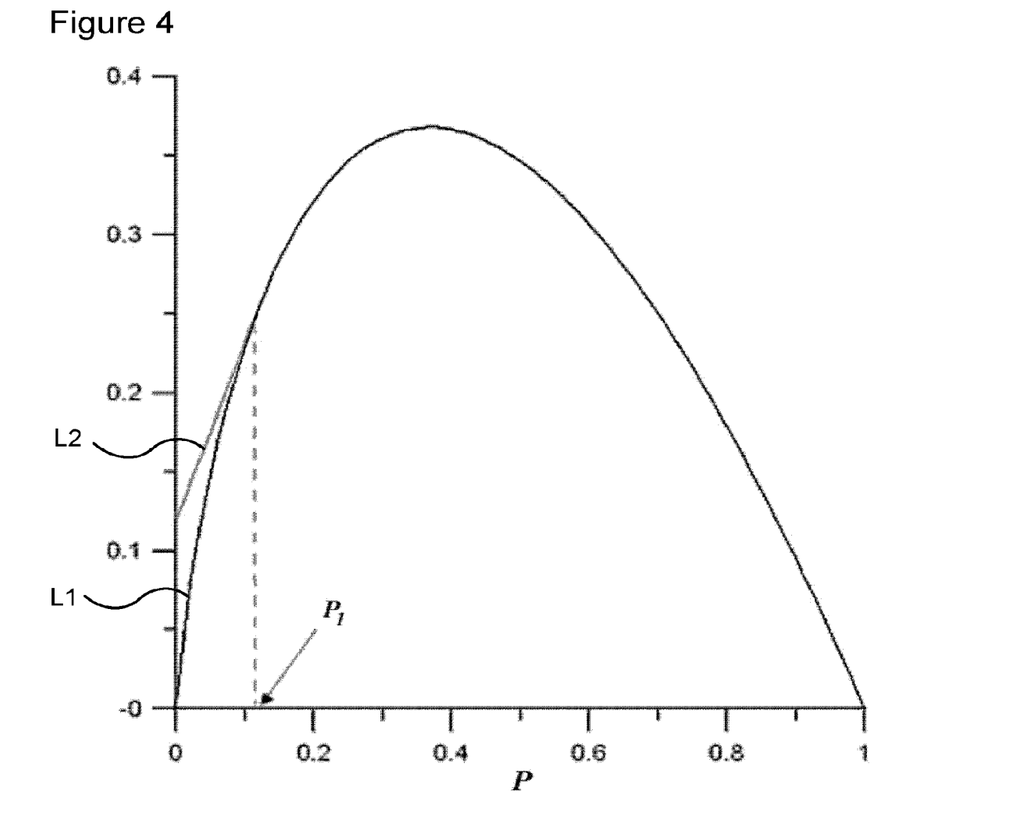
FIG. 4 shows a plot of a novel scattering function.

The fourth step S108 of method 100 uses the current primary beam estimate $P^n(x, y, \theta)$ to update the estimate of the scatter $S^n(x, y, \theta)$ using the expression $$S^n(x,y,\theta)=SF(P^n(x,y,\theta))*G_2(X,y),$$

where $SF(\bullet)$ is the scatter function, the symbol "*" represents a convolution operator, and $$G_2(x,y)=A_1\exp[-\alpha_1(x^2+y^2)]+A_2\exp[-\alpha_2(x^2+y^2)]$$

is smoothing function that is a double Gaussian kernel with one term representing the coherent (Rayleigh) scattering and the other term representing the incoherent (Compton) scattering. The scatter function $SF(\bullet)$ is discussed herein with regards to FIG. 4.

The fifth step S110 of method 100 inquiries whether the primary beam estimate $P^n(x, y, \theta)$ has converged by inquiring whether predefined convergence criteria have been satisfied. For example, the convergence criterion can be whether a Banach space distance measure of the difference between the current and previous primary beam estimates (e.g., the root mean square of the difference) is less than a predefined value. If the convergence criteria are satisfied the method 100 proceeds to step S112. Otherwise, the method 100 loops back to step S104 to update the estimates of the scatter and primary beam.

The final step S112 of the method 100 reports the current value of the primary-beam estimate $P^n(x, y, \theta)$ as the final value of the primary beam. The current value of the scatter $S^n(x, y, \theta)$ can also be reported if it is used in the image reconstruction process or in other post-processing algorithms.

Figure 2:
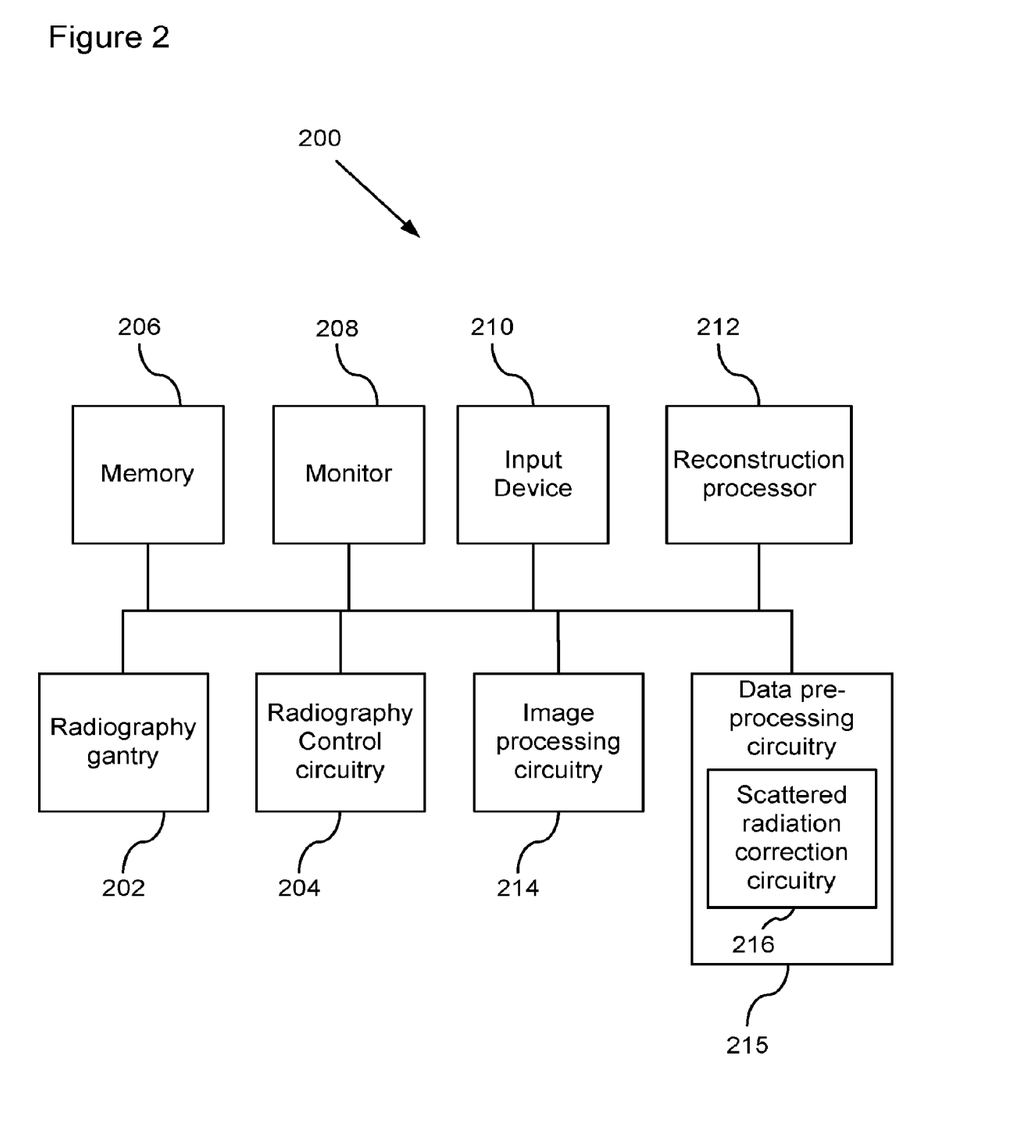
FIG. 2 shows a schematic of an implementation of a computed tomography system.

In one implementation, for each new projection angle $\theta+\Delta\theta$ method 100 stores the previous scatter value $S_{prev}=S^n(x, y, \theta)$ at the conclusion of the previous scatter correction calculation. The previous scatter value is then used to initiate the current scatter correction calculation $S^0(x, y, \theta+\Delta\theta)=S_{prev}$. Because the difference between projection angles will typically be small, using previous scatter value $S_{prev}$ to initiate the current scatter correction calculation will often result in quicker convergence than starting each scatter correction calculation assuming no scatter, i.e., $S^0(x, y, \theta+\Delta\theta)=0$ FIG. 2 shows an arrangement of an X-ray diagnostic apparatus 200. The X-ray diagnostic apparatus 200 comprises a radiography gantry 202, radiography control circuitry 204, memory 206, monitor 208, input device 210, reconstruction processing circuitry 212, image processing circuitry 214, and scattered radiation correction circuitry 216 that is a subset of the data pre-processing circuitry 215, where the term "circuitry" can be interpreted as a Central Processing Unit (CPU) executing program instructions or as special-purpose hardware circuitry, such as an FPGA, or other specialized circuitry. In one implementation, the data from the X-ray diagnostic apparatus 200 can be processed approximately in chronological order with data pre-processing circuitry 215 processing the data first to prepare the data for reconstruction using computed tomography. Next, the reconstruction processing circuitry 212 operates on the pre-processed data in the projection domain to create an image expressing the absorption in each image voxel (a volume pixel). Next, the reconstructed image can be post-processed using the image processing circuitry 214 to render the image, filter/smooth the image, add false coloring to the image, etc. In one implementation, there can be overlap among the data processing between the processing of the reconstruction processing circuitry 212, image processing circuitry 214, and data pre-processing circuitry 215. For example, the image processing circuitry 214 could overlap with the reconstruction processing circuitry 212, wherein the image processing also includes additional processing steps during the CT reconstruction algorithm.

Figure 3:
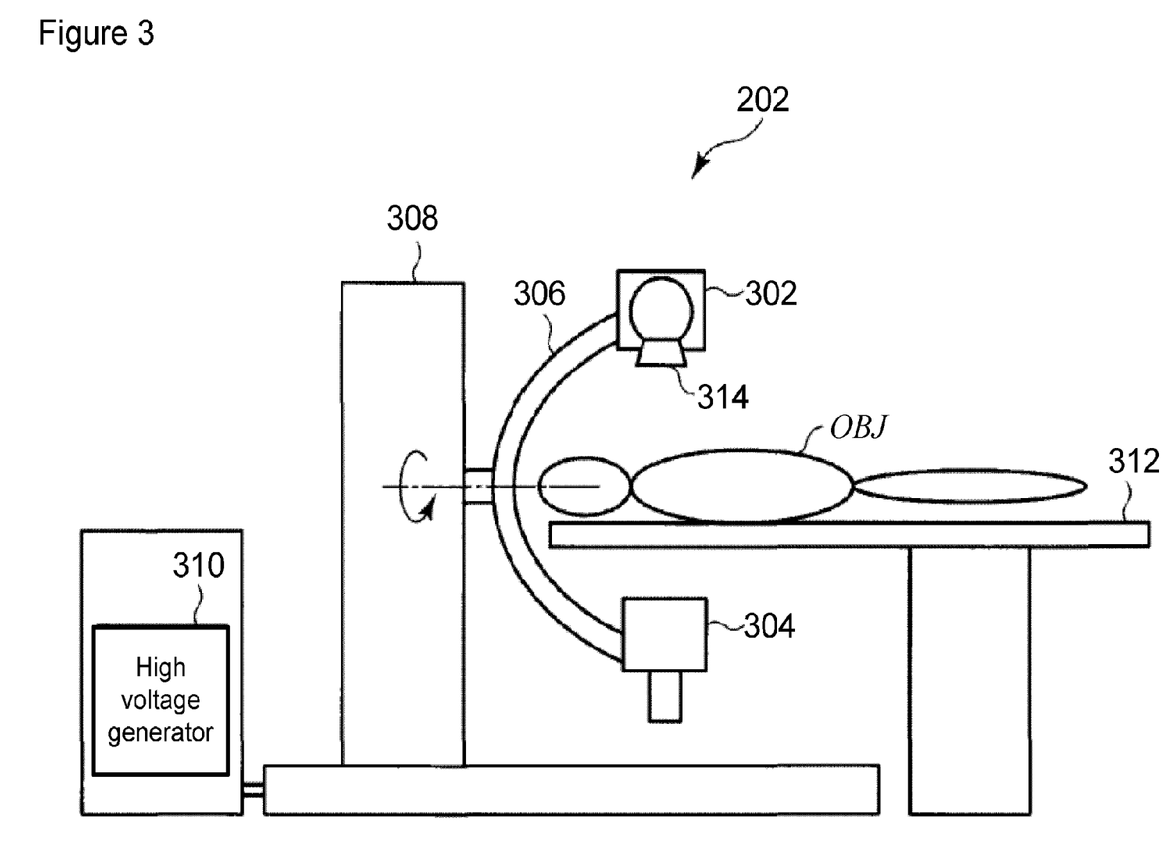
FIG. 3 shows an implementation of a computed tomography system.

FIG. 3 shows a non-limiting example of the outer appearance of the radiography gantry 202. As shown in FIG. 3, the radiography gantry 202 includes an X-ray tube 302, X-ray detector 304, C-arm 306, stand 308, high voltage generator 310, bed 312, and X-ray stop device 314. FIG. 3 is one example of a CT system for which the scatter correction method can be used. The scatter correction method can also be applied to other X-ray imaging geometries used for CT imaging, including diagnostic CT systems, intervention CT systems, systems using photon-integrating detectors, systems using photon-integrating detectors, cardiac, head, and full body scanners, spinning-tube CT scanners, multi-slice CT systems, for example. Furthermore, the method of scatter suppression and correction discussed herein applies also to projective measurements, such as radiographic and fluoroscopic imaging, that are not used for CT reconstruction. That is, the method of scatter suppression and correction are applicable to any X-ray projective measurements regardless of the intended use of the projective measurements, whether the projection images are an end in themselves, or they are for CT reconstruction, or they are intended for some other purpose.

The high voltage generator 310 generates a high voltage to be applied between the electrodes of the X-ray tube 302, and also generates a filament current to be supplied to the cathode filament of the X-ray tube 302. Upon receiving the high voltage and filament current, the X-ray tube 302 generates X-rays. The X-ray stop device 314 shapes X-rays generated by the X-ray tube 302. The X-ray detector 304 can be a two-dimensional array of a plurality of detection elements (pixels) that directly or indirectly convert incident X-rays into electric charges. The X-ray tube 302 is mounted on, for example, one end of the floor type C-arm 306. The X-ray detector 304 is mounted on the other end of the C-arm 306. The X-ray detector 304 faces the X-ray tube 302 through an object OBJ to be examined which is placed on the bed 312. The C-arm 306 is rotatably supported on the stand 308. Repeating radiography with respect to the object OBJ while rotating the C-arm 306 makes it possible to acquire X-ray images (projection data) in many directions which are required for three-dimensional image reconstruction.

The radiography control circuitry 204 controls the rotation of the C-arm 306, the application of high voltages from the high voltage generator 310 to the X-ray tube 302, and reading of signals from the X-ray detector 304 in order to execute rotational radiography and generate X-ray image data.

The memory 206 stores a dedicated program for executing the scattered radiation correction method 100.

The monitor 208 is a display device such as a CRT, plasma display, or liquid crystal display which displays an X-ray diagnostic image or the like in a predetermined form in accordance with a signal received from the reconstruction processing circuitry 212 or the image processing circuitry 214.

The input device 210 includes a keyboard, various kinds of switches, a mouse, and the like and is used to input a radiography instruction, image selection instruction, etc. The reconstruction processor 212 reconstructs volume data from projection images in a plurality of projection directions.

The image processing circuitry 214 executes predetermined image processing such as volume rendering processing and image difference processing as needed.

The scattered radiation correction circuitry 216 implements the scattered radiation correction method 100. The scattered radiation correction circuitry 216 implements the scatter correction method 100 to extract the primary beam X-ray projection data $P^{Final}(x, y, \theta)$ from the measured X-ray projection data $T(x, y, \theta)$ with scatter.

FIG. 4, shows a conventional (L1) and a novel (L2) scattering function to be used in the method 100. Using a forward scatter model that ignores multiple scattering and the polychromatic nature of the incident x-ray beam and the scattered x-ray beam, the conventional scatter function is given by $$SF(x) = -x \log x,$$

where log is the natural logarithm function. This conventional scatter function model is shown as line L1 in FIG. 4. While this conventional scattering model works well for many CT applications, in certain CT applications (e.g., in large field-of-view scans in which there is secondary scatter from a bowtie filter and other scatter sources) dark-band artifacts can manifest in the reconstructed CT image. For example, these dark-band artifacts can be observed in the shoulder region of a head and shoulder image. These dark-band artifacts can be mitigated by using the scatter function model shown as line L2 in FIG. 4.

FIG. 4 shows a plot of two scatter function models, L1 and L2, as a function of the primary beam transmission P, where the primary beam transmission is plotted along the horizontal axis and the scatter function is plotted along the vertical axis. In the limit of small primary beam transmission, the assumptions upon which the conventional scatter function L1 is based (e.g., single scattering and small scattering angle) lead to the results that the scatter linearly approaches zero as the primary beam transmission goes to zero. However, as an empirical matter, there can still be residual scatter even as the primary beam becomes vanishingly small. Therefore a scatter function model such as L2, where the scatter function remains is greater than zero as the primary beam transmission approaches zero, more accurately models the scatter that is observed in certain implementations of CT imaging. The scatter function model L2 can be expressed as $$SF(P) = \begin{cases} -(\log(P_1)+1)P + P_1 & P < P_1 \\ -P\log(P) & P \geq P_1 \end{cases},$$

and $P_1$ is a predefined value chosen to match empirical scatter measurements and/or that minimizes dark-band artifacts. Using L2 rather than L1 as the scatter function in the scatter correction calculation can result in fewer dark-band artifacts. In another implementation, the scatter function can be any predetermined function that predicts observed X-ray scatter and for which the scatter is greater than zero in the limit that the primary beam transmission goes to zero.

Figure 5:
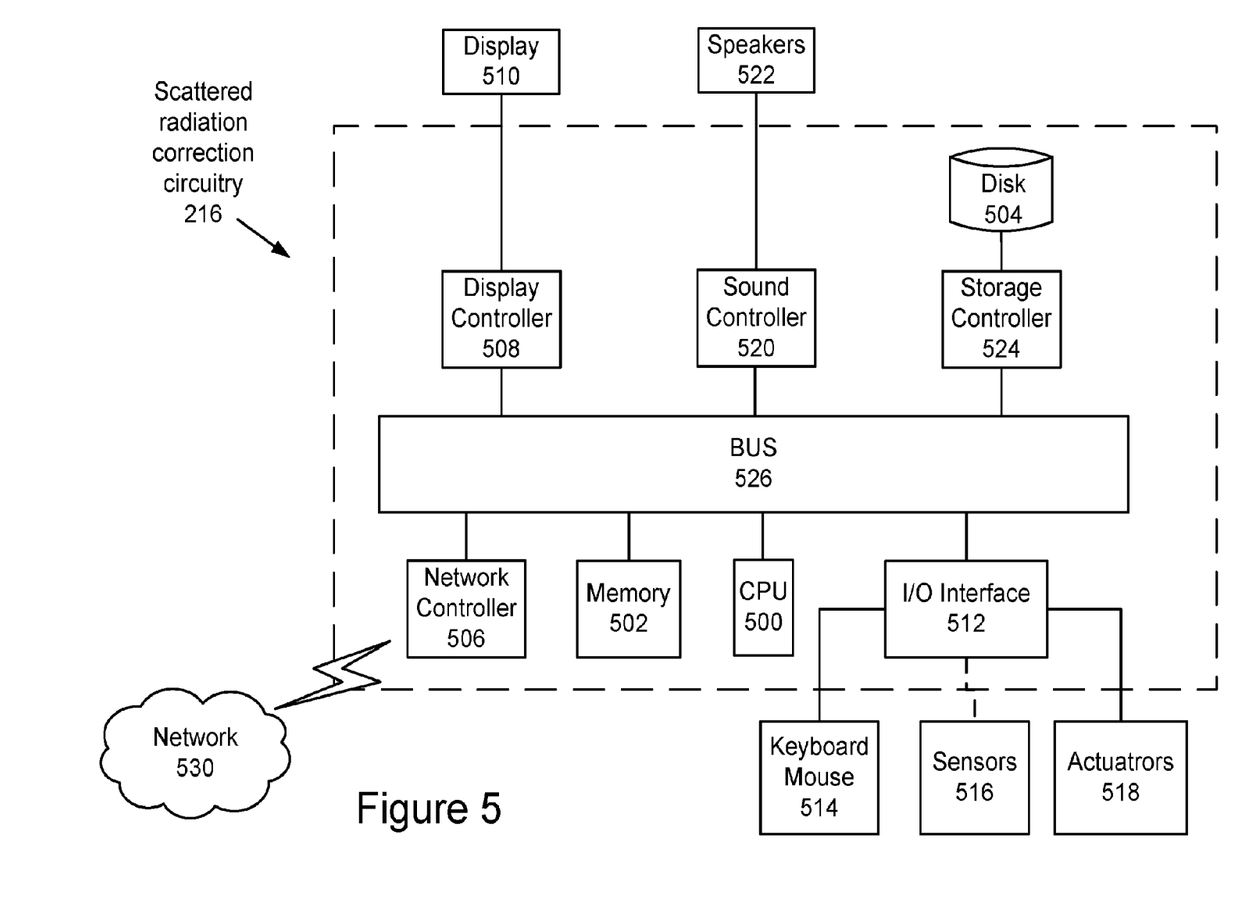
FIG. 5 shows a schematic diagram of an implementation of scattered radiation correction circuitry.

FIG. 5 shows an implementation of the scattered radiation correction circuitry 216 that performs the method 100. Next, a hardware description of the scattered radiation correction circuitry 216 according to exemplary embodiments is described with reference to FIG. 5. In one implementation, the hardware, which performs the function of the scattered radiation correction circuitry 216, can also perform additional functions, including the functions of the radiography control circuitry 204, the reconstruction processor 212, and the image processing circuitry 214. These functions can be performed using a single instance of the hardware shown in FIG. 5, or separate functions can be performed by separate instances of the hardware shown in FIG. 5, which are each part of a single network.

In FIG. 5, the scattered radiation correction circuitry 216 includes, e.g., a CPU 500 which performs the processes described herein. Alternatively, the scattered radiation correction circuitry 216 is a specialized hardware circuitry other than a CPU. Process data and instructions may be stored in memory 502. Processes and instructions may also be stored on a storage medium disk 504 such as a hard drive (HDD) or portable storage medium or may be stored remotely. Further, this disclosure is not limited by the form of the computer-readable media on which the instructions are stored. For example, the instructions may be stored on CDs, DVDs, in FLASH memory, RAM, ROM, PROM, EPROM, EEPROM, hard disk or any other information processing device with which the scattered radiation correction circuitry 216 communicates, such as a server or computer.

Further, aspects of this disclosure may be provided as a utility application, background daemon, or component of an operating system, or combination thereof, executing in conjunction with CPU 500 and an operating system such as Microsoft Windows 7, UNIX, Solaris, LINUX, Apple MAC-OS and other systems known to those skilled in the art.

CPU 500 may be a Xenon or Core processor from Intel of America or an Opteron processor from AMD of America, or may be other processor types that would be recognized by one of ordinary skill in the art, such as an ARM-based processor. Alternatively, the CPU 500 may be implemented on an FPGA, ASIC, PLD or using discrete logic circuits, as one of ordinary skill in the art would recognize. Further, CPU 500 may be implemented as multiple processors cooperatively working in parallel to perform the instructions of the inventive processes described above.

The scattered radiation correction circuitry 216 in FIG. 5 also includes a network controller 506, such as an Intel Ethernet PRO network interface card from Intel Corporation of America, for interfacing with network 530. As can be appreciated, the network 530 can be a public network, such as the Internet, or a private network such as an LAN or WAN network, or any combination thereof and can also include PSTN or ISDN sub-networks. The network 530 can also be wired, such as an Ethernet network, or can be wireless such as a cellular network including EDGE, 3G and 4G wireless cellular systems. The wireless network can also be WiFi, Bluetooth, or another wireless form of communication.

The scattered radiation correction circuitry 216 further includes a display controller 508, such as a NVIDIA GeForce GTX or Quadro graphics adaptor from NVIDIA Corporation of America that respectively interface with a corresponding display 510, such as a Hewlett Packard HPL2445w LCD monitor.

The scattered radiation correction circuitry 216 further includes a general purpose I/O interface 512 interfaces with a keyboard and/or mouse 514 as well as sensors 516. The general purpose I/O interface 512 can also connect to a variety of actuators 518. The general purpose I/O interface 512 can also connect to a variety of peripherals including printers and scanners, such as an OfficeJet or DeskJet from Hewlett Packard.

A sound controller 520 is also provided in the scattered radiation correction circuitry 216, such as Sound Blaster X-Fi Titanium from Creative, to interface with speakers/microphone 522 thereby providing sounds and/or music.

The general purpose storage controller 524 connects the storage medium disk 504 with communication bus 526, which may be an ISA, EISA, VESA, PCI, or similar, for interconnecting all of the components of the scattered radiation correction circuitry 216. A description of the general features and functionality of the display 510, keyboard and/or mouse 514, as well as the display controller 508, storage controller 524, network controller 506, sound controller 520, and general purpose I/O interface 512 is omitted herein for brevity as these features are known.

Figure 6:
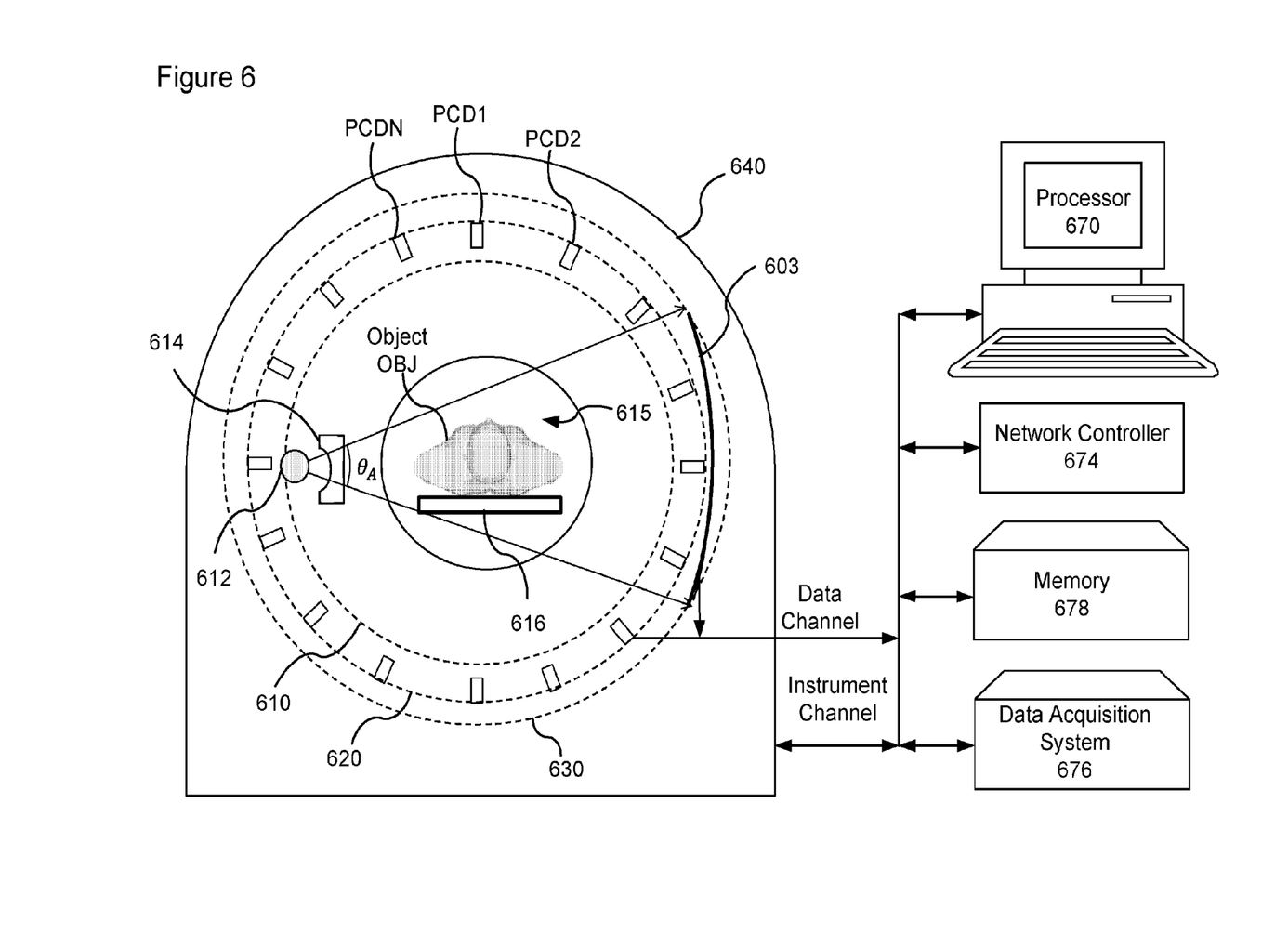
FIG. 6 shows a schematic of an implementation of a computed tomography system including both energy integrating detectors and photon-counting detectors.

FIG. 6 shows a schematic view of a CT scanner system having energy integrating detectors arranged in a third generation geometry and photon counting detectors (PCDs) arranged in a fourth-generation geometry. FIG. 6 shows a coupled ring topology with the X-ray source 614 inside the ring of PCDs and the X-ray detector unit 603 is outside the ring of PCDs, as discussed in U.S. patent application Ser. No. 13/426,903, incorporated herein by reference in its entirety.

Illustrated in FIG. 6 is an implementation for placing the photon-counting detectors (PCDs) in a predetermined fourth-generation geometry in combination with a detector unit 603 in a predetermined third-generation geometry in a CT scanner system. The diagram illustrates relative positions among an object OBJ to be scanned resting on a table 616, an X-ray source 612, a collimator/filter 614, an X-ray detector 603, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy integrating detectors in the X-ray detector 603.

Also shown in FIG. 6 is circuitry and hardware for acquiring, storing, processing, and distributing X-ray projection data. The circuitry and hardware include: a processor 670, a network controller 674, a memory 678, and a data acquisition system 676. In one implementation, the scatter correction could be performed using a dedicated program stored in memory 678 and loaded into the processor 670, which then performs the scatter correction on the projection data before the image reconstruction steps. In one implementation, the scatter correction is performed in circuitry associated with the data acquisition system 676 before the projection data is stored into memory 678 for later processing.

In one implementation, the X-ray source 612 and the collimator/filter 614 are fixedly connected to a rotational component 610 that is rotatably connected to a gantry 640. The X-ray detector 603 is similarly fixedly connected to a rotational component 630 that is rotatably connected to the gantry 640. The PCDs are fixedly connected to a circular component 620 that is fixedly connected to the gantry 640. The gantry 640 houses many pieces of the CT scanner.

The gantry of the CT scanner also includes an open aperture 615 enabling the object OBJ that is arranged on a table 616 positioned in a projection plane of the X-rays traveling from the X-ray source to the PCDs and detector unit 603. The "projection plane" is a volume wherein X-rays pass from the X-ray source 612 to the detectors including the PCDs and the detector unit 603. The "object space" is the intersection of the projection plane and the open aperture 615 of the gantry. The "object space" includes the union of projection planes corresponding to all projection angles of the X-ray source 612 as the X-ray source 612 rotates around the aperture of the gantry.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 6 includes a detector unit 603 having energy-integrating detectors arranged in a conventional third-generation geometry. The detector elements in the detector unit 603 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined second circular component 620 in a gantry. In one implementation, the photon-counting detectors PCD1 through PCDN are fixedly placed on the circular component 620 at predetermined equidistant positions. In an alternative implementation, the photon-counting detectors PCD1 through PCDN are fixedly placed on the circular component 620 at predetermined non-equidistant positions. The circular component 620 remains stationary with respect to the object OBJ and does not rotate during the data acquisition.

Both the X-ray source 612, collimator 614 (e.g., a bow tie filter), and the detector unit 603 rotate around the object OBJ while the photon-counting detectors PCD1 through PCDN are stationary with respect to the object OBJ. In one implementation, the X-ray source 612 projects X-ray radiation with a predetermined source fan beam angle $\theta_A$ towards the object OBJ while the X-ray source 612 rotates around the object OBJ outside the sparsely placed photon-counting detectors PCD1 through PCDN. Furthermore, the detector unit 603 is mounted at a diametrically opposed position from the X-ray source 612 across the object OBJ and rotates outside the stationary circular component 620, on which the photon-counting detectors PCD1 through PCDN are fixed in a predetermined sparse arrangement.

In one implementation, the X-ray source 612 optionally travels a helical path relative to the object OBJ, wherein the table 616 moves the object OBJ linearly in a predetermined direction perpendicular to the rotational plane of the rotating portion 610 as the rotating portion 610 rotates the X-ray source 612 and detector unit 603 in the rotational plane.

The motion of the rotating portion 610 around the object OBJ is controlled by a motion control system. The motion control system can be integrated with a data acquisition system or can be separate providing one way information regarding the angular position of the rotating portion 610 and the linear position of the table 616. The motion control system can include position encoders and feedback to control the position of the rotating portion 610 and the table 616. The motion control system can be an open loop system, a closed loop system, or a combination of an open loop system and a closed loop system. The motion control system can use linear and rotary encoders to provide feedback related to the position of the rotating portion 610 and the position of the table 616. The motion control system can use actuators to drive the motion of the rotating portion 610 and the motion of the table 616. These positioners and actuators can include: stepper motors, DC motors, worm drives, belt drives, and other actuators known in the art.

The CT scanner also includes a data channel that routes projection measurement results from the photon counting detectors and the detector unit 603 to a data acquisition system 676, a processor 670, memory 678, network controller 674. The data acquisition system 676 controls the acquisition, digitization, and routing of projection data from the detectors. The data acquisition system 676 also includes radiography control circuitry to control the rotation of the annular rotating frames 610 and 630. In one implementation data acquisition system 676 will also control the movement of the bed 616, the operation of the X-ray source 612, and the operation of the X-ray detectors 603. The data acquisition system 676 can be a centralized system or alternatively it can be a distributed system. In an implementation, the data acquisition system 676 is integrated with the processor 670. The processor 670 performs functions including reconstructing images from the projection data, pre-reconstruction processing of the projection data, and post-reconstruction processing of the image data.

The pre-reconstruction processing of the projection data can include correcting for detector calibrations, detector nonlinearities, polar effects, noise balancing, and material decomposition.

Post-reconstruction processing can include filtering and smoothing the image, volume rendering processing, and image difference processing as needed. The image reconstruction process can be performed using filtered back projection, iterative image reconstruction methods, or stochastic image reconstruction methods. Both the processor 670 and the data acquisition system 676 can make use of the memory 676 to store, e.g., projection data, reconstructed images, calibration data and parameters, and computer programs.

The processor 670 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 678 can be a hard disk drive, CD-ROM drive, DVD drive, FLASH drive, RAM, ROM or any other electronic storage known in the art.

The network controller 674, such as an Intel Ethernet PRO network interface card from Intel Corporation of America, can interface between the various parts of the CT scanner. Additionally, the network controller 674 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 612 is optionally a single energy source. In another implementation, the X-ray source 612 is configured to perform a kV-switching function for emitting X-ray radiation at a predetermined high-level energy and at a predetermined low-level energy. In still another alternative embodiment, the X-ray source 612 is a single source emitting a broad spectrum of X-ray energies. In still another embodiment, the X-ray source 612 includes multiple X-ray emitters with each emitter being spatially and spectrally distinct.

The detector unit 603 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), BaF$_2$, CaF$_2$ (Eu), ZnS(Ag), CaWO$_4$, CdWO$_4$, YAG(Ce), Y$_3$Al$_5$O$_{12}$(Ce), GSO, LSO, LaCl$_3$(Ce), LaBr$_3$(Ce), LYSO, BGO, LaCl$_3$ (Ce), LaBr$_3$(Ce), C$_{14}$H$_{10}$, C$_{14}$H$_{12}$, and C$_{10}$H$_8$), an organic liquid (e.g., an organic solvent with a fluor such as p-terphenyl (C$_{18}$H$_{14}$), PBD (C$_{20}$H$_{14}$N$_2$O), butyl PBD (C$_{24}$H$_{22}$N$_2$O), or PPO (C$_{15}$H$_{11}$NO)), a plastic (e.g., a flour suspended in a solid polymer matrix), or other know scintillators or phosphors.

The PCDs can use a direct X-ray radiation detectors based on semiconductors, such as cadmium telluride (CdTe), cadmium zinc telluride (CZT), silicon (Si), mercuric iodide (HgI$_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

While certain embodiments have been described, these embodiments have been presented by way of example only, and are not intended to limit the scope of the inventions. Indeed, the novel methods, apparatuses and systems described herein may be embodied in a variety of other forms; furthermore, various omissions, substitutions and changes in the form of the methods, apparatuses and systems described herein may be made without departing from the spirit of the inventions. The accompanying claims and their equivalents are intended to cover such forms or modifications as would fall within the scope and spirit of the inventions.

The invention claimed is:

1. An apparatus for scatter correction of projection data, the apparatus comprising:
   processing circuitry configured to
   calculate a primary-beam estimate P″, and
   calculate a scatter estimate S″ using a convolution between a scattering function, SF(P″), and a smoothing function G,
   wherein P″ is a current primary-beam estimate, S″ is a current scatter estimate, and SF(P″) is a predetermined scatter function that is a function of the current the primary-beam estimate and is greater than zero over the range $0 \leq P'' < 1$.

2. The apparatus according to claim 1, wherein the processing circuitry is further configured to calculate the primary-beam estimate P″ as a ratio having a product of a previous value of the primary-beam estimate P″$^{-1}$ with the projection data T in the numerator and a sum of the previous value of the primary-beam estimate P″$^{-1}$ with a previous value of the scatter estimate S″$^{-1}$ in the denominator.

3. The apparatus according to claim 2, wherein the processing circuitry is further configured to calculate the scatter estimate S″ using a scatter function SF(P″), wherein when the primary-beam estimate P″ is less than a predefined value P$_1$ that is between zero and one, the scatter function SF(P″) is a linear function, the linear function having a non-zero value when the value of the primary-beam estimate P″ is zero, and when the primary-beam estimate P″ is equal to or greater than the predefined value P$_1$, the scatter function SF(P″) includes a product of the primary-beam estimate P″ with a logarithm of the primary-beam estimate P″.

4. The apparatus according to claim 3, wherein the processing circuitry is further configured to calculate the scatter estimate using the smoothing function G that is a double Gaussian kernel representing both coherent scattering processes and incoherent scattering processes.

5. The apparatus according to claim 1, wherein the processing circuitry is further configured to perform an iterative loop, wherein each iteration of the iterative loop includes the calculation of the primary-beam estimate and the calculation of the scatter estimate.

6. The apparatus according to claim 5, wherein the processing circuitry is further configured to stop the iterative loop when a predefined convergence criterion is satisfied.

7. A method of correcting for scatter in projection data using processing circuitry, the method comprising:
   calculating, by the processing circuitry, a primary-beam estimate P″;

calculating a scatter estimate $S''$ using a convolution between a scattering function of the primary-beam estimate, $SF(P'')$, and a smoothing function G, wherein $P''$ is a current value of the primary-beam estimate, $S''$ is a current value of the scatter estimate, and $SF(P'')$ is a predetermined scatter function that is a function of the current primary-beam estimate and is greater than zero over the range $0 \leq P'' < 1$.

8. The method according to claim 7, wherein the step of calculating the primary-beam estimate $P''$ as a ratio having a product of a previous value of the primary-beam estimate $P''^{-1}$ with the projection data T in the numerator and a sum of the previous value of the primary-beam estimate $P''^{-1}$ with a previous value of the scatter estimate $S''^{-1}$ in the denominator.

9. The method according to claim 8, wherein the step of calculating the scatter estimate $S''$ using a scatter function $SF(P'')$, wherein when the primary-beam estimate $P''$ is less than a predefined value $P_1$ that is between zero and one, the scatter function $SF(P'')$ is a linear function, the linear function having a non-zero value when the value of the primary-beam estimate $P''$ is zero, and when the primary-beam estimate $P''$ is equal to or greater than the predefined value $P_1$, the scatter function $SF(P'')$ includes a product of the primary-beam estimate $P''$ with a logarithm of the primary-beam estimate $P''$.

10. The method according to claim 9, wherein the step of calculating the scatter estimate includes using the smoothing function G that is a double Gaussian kernel representing both coherent scattering processes and incoherent scattering processes.

11. The method according to claim 7, further comprising repeating the steps of calculating the primary-beam estimate and calculating the scatter estimate value in an iterative loop.

12. The method according to claim 11, further comprising stopping the iterative loop when a predetermined convergence criterion has been satisfied.

13. An imaging apparatus for computed tomography, comprising:
a radiation source configured to emit radiation toward an image object;
a radiation detector configured to detect the radiation transmitted from the radiation source and through the image object to generate projection data representing an intensity of the radiation at the radiation detector; and
scatter-correction processing circuitry configured to
calculate a primary-beam estimate $P''$ using the projection data, wherein $P''$ is a current value of the primary-beam estimate, and
calculate a scatter estimate $S''$ using a convolution between a scattering function of the primary-beam estimate $SF(P'')$ and a smoothing function G, wherein $S''$ is a current value of the scatter estimate, and $SF(P'')$ is a predetermined scatter function that is a function of the current primary-beam estimate and is greater than zero over the range $0 \leq P'' < 1$; and
image-reconstruction processing circuitry configured to reconstruct a tomographic image from the primary-beam estimate.

14. The apparatus according to claim 13, wherein the scatter-correction processing circuitry is further configured to calculate primary-beam estimate $P''$ as a ratio having the product of a previous value of the primary-beam estimate $P''^{-1}$ with the projection data T in the numerator and a sum of the previous value of the primary-beam estimate $P''^{-1}$ with a previous value of the scatter estimate $S''^{-1}$ in the denominator.

15. The apparatus according to claim 14, wherein the scatter-correction processing circuitry is configured to calculate the scatter estimate $S''$ using a scatter function $SF(P'')$, wherein when the primary-beam estimate $P''$ is less than a predefined value $P_1$ that is between zero and one, the scatter function $SF(P'')$ is a linear function, the linear function having a non-zero value when the value of the primary-beam estimate $P''$ is zero, and when the primary-beam estimate $P''$ is equal to or greater than the predefined value $P_1$, the scatter function $SF(P'')$ includes a product of the primary-beam estimate $P''$ with a logarithm of the primary-beam estimate $P''$.

16. The apparatus according to claim 15, wherein the scatter-correction processing circuitry is configured to calculate the scatter estimate using the smoothing function G, which is a double Gaussian kernel representing both coherent scattering processes and incoherent scattering processes.

17. The apparatus according to claim 13, wherein the image-reconstruction processing circuitry is further configured to reconstruct a tomographic image from the primary-beam estimate using one of a filtered backprojection method, a Fourier-transform-based image reconstruction method, and an iterative image reconstruction method.

18. The apparatus according to claim 13, wherein the scatter correction processing circuitry is further configured to perform an iterative loop that stops when a predetermined convergence criterion is satisfied, wherein each iteration of the iterative loop includes the calculation of the primary-beam estimate and the calculation of the scatter estimate.

* * * * *